(12) United States Patent
Eilert et al.

(10) Patent No.: US 6,228,404 B1
(45) Date of Patent: May 8, 2001

(54) METHOD AND APPARATUS FOR DETERMINING THE LEAN CONTENT OF MEAT PRODUCTS

(75) Inventors: Scott Eilert; Brian Wayne Bell, both of Wichita, KS (US)

(73) Assignee: Excel Corporation, Wichita, KS (US)

( * ) Notice: Subject to any disclaimer, the term of this patent is extended or adjusted under 35 U.S.C. 154(b) by 0 days.

(21) Appl. No.: 09/503,594

(22) Filed: Feb. 11, 2000

(51) Int. Cl.⁷ ........................................ G01N 27/02
(52) U.S. Cl. .................. 426/231; 426/237; 436/149; 324/439
(58) Field of Search .................. 426/231, 645, 426/237; 436/149; 324/439

(56) References Cited

U.S. PATENT DOCUMENTS

| | | | |
|---|---|---|---|
| 3,735,247 | * 5/1973 | Harker | 324/226 |
| 4,496,907 | 1/1985 | Funk et al. | 324/445 |
| 4,534,229 | 8/1985 | Funk et al. | 73/863 |
| 4,727,330 | 2/1988 | Funk | 324/445 |
| 5,189,366 | * 2/1993 | Mayo | 324/233 |
| 5,289,123 | * 2/1994 | Bublitz et al. | 324/263 |

* cited by examiner

Primary Examiner—Nina Bhat
(74) Attorney, Agent, or Firm—Dorsey & Whitney LLP

(57) ABSTRACT

A method and apparatus for determining the approximate lean content of pork bellies, and a method for categorizing pork bellies on the basis of weight and lean content is described. The method for determining approximate lean content uses a conductivity apparatus configured and arranged to apply an electromagnetic field to the pork belly. The approximate lean content of the pork belly is determined on the basis of a relationship between the measured conductivity of the pork belly and the fat content of the pork belly. A system for categorizing pork bellies on the basis of weight and lean content is also described.

17 Claims, 5 Drawing Sheets

METHOD AND APPARATUS FOR DETERMINING THE LEAN CONTENT OF MEAT PRODUCTS

FIELD OF THE INVENTION

The present invention is directed to methods and apparatuses for determining the characteristics of meat products. More particularly, the invention is directed to methods and apparatuses for determining the lean content of pork products, including pork bellies.

BACKGROUND OF THE INVENTION

When pigs are fabricated, pork bellies are one of the cuts of meat obtained from the underside of the pig. Pork bellies are traditionally sold in a fresh, uncured state to bacon processors, who subsequently trim and slice them into strips to form bacon. Prior to being sold to bacon processors, the majority of these bellies are graded, sorted, and priced on the basis of weight.

Although this traditional method of grading, sorting, and pricing pork bellies based upon weight has been in use for years, it has certain significant limitations. One of the greatest limitations is that pork bellies having the same weight can have widely varying fat content. This varying fat content is problematic because many consumers are concerned about fat content as a determinant of quality. These consumers are reluctant to buy a pork product that has a fat content varying from their expectations, and would benefit from a grading system that considers not only the weight of the pork belly or bacon product, but also the portion of the belly or bacon that is not fat (also referred to as "lean content"). Unfortunately, the lean content of a meat product is difficult to measure because fat is normally integrated with the muscle, and thus not readily apparent to the eye. Although small samples of bellies can be collected and analyzed to determine fat content, such methods are normally slow, tedious, and cause damage to the belly.

Therefore, a need exists for a method and apparatus for easily, inexpensively, and quickly determining the lean content of pork bellies. A further need exists for a method and apparatus to sort pork bellies on the basis of features other than simply weight. The methods and apparatus should allow bacon processors to identify and market bacon with a consistent lean content. Also, the methods should allow lean content measurements to be made in a non-invasive and non-destructive manner that is both fast and cost effective.

SUMMARY OF THE INVENTION

The present invention is directed to a method and apparatus for determining the approximate fat content of pork bellies, and a method for categorizing pork bellies on the basis of weight and lean content. The method for determining approximate lean content includes providing a pork belly, providing a conductivity apparatus configured and arranged to apply an electromagnetic field to the pork belly, applying an electromagnetic field to the pork belly with the conductivity apparatus, measuring the conductivity of the pork belly with the conductivity apparatus as the electromagnetic field is applied, and determining the approximate lean content of the pork belly on the basis of a relationship between the measured conductivity of the pork belly and the actual lean content of the pork belly.

In certain implementations, the approximate lean content of the pork belly is related to measured conductivity on the basis of the following equation:

$$L = I + (C\sqrt{P})$$

wherein "L" is the approximate lean content of the pork belly in percent, "I" is the intercept coefficient from the conductivity measurement, "C" is the correlation coefficient from the conductivity measurement, and "P" is the phase mean average conductivity from the conductivity measurement. "I" is typically from about −3.0 to −2.0, frequently from about −2.1 to −2.5, and can be approximately −2.35. "C" is typically from about 1.0 to 3.0, frequently about 1.5 to 2.0, and can be approximately 1.8.

The invention is also directed to a method of categorizing pork bellies. In one implementation, the method includes providing a plurality of pork bellies; providing a conductivity sensor configured and arranged to apply an electromagnetic field to individual pork bellies; sequentially placing each pork belly of the plurality of pork bellies into the conductivity sensor; sequentially measuring the conductivity of each pork belly of the plurality of pork bellies using the conductivity sensor; determining the approximate fat content of each pork belly on the basis of a relationship between the measured conductivity of the pork belly and the fat content of the pork belly; and categorizing each pork belly of the plurality of pork bellies on the basis of fat content or lean content.

The step of providing a conductivity sensor typically includes providing a conductivity sensor having a receptacle configured to receive a pork belly; an electromagnetic field generator configured to generate an electromagnetic field through a pork belly positioned within the receptacle; and a sensor configured to measure changes in the electromagnetic field resulting from the presence of the pork belly. The receptacle can be configured to bend the pork belly upon insertion into the receptacle, or can be configured to receive a pork belly bent into a substantially crescent shape.

The above summary of the present invention is not intended to describe each disclosed embodiment of the present invention. This is the purpose of the figures and the detailed description that follow.

BRIEF DESCRIPTION OF THE DRAWINGS

Other aspects and advantages of the invention will become apparent upon reading the following detailed description and upon reference to the drawings in which.

Figure 1:
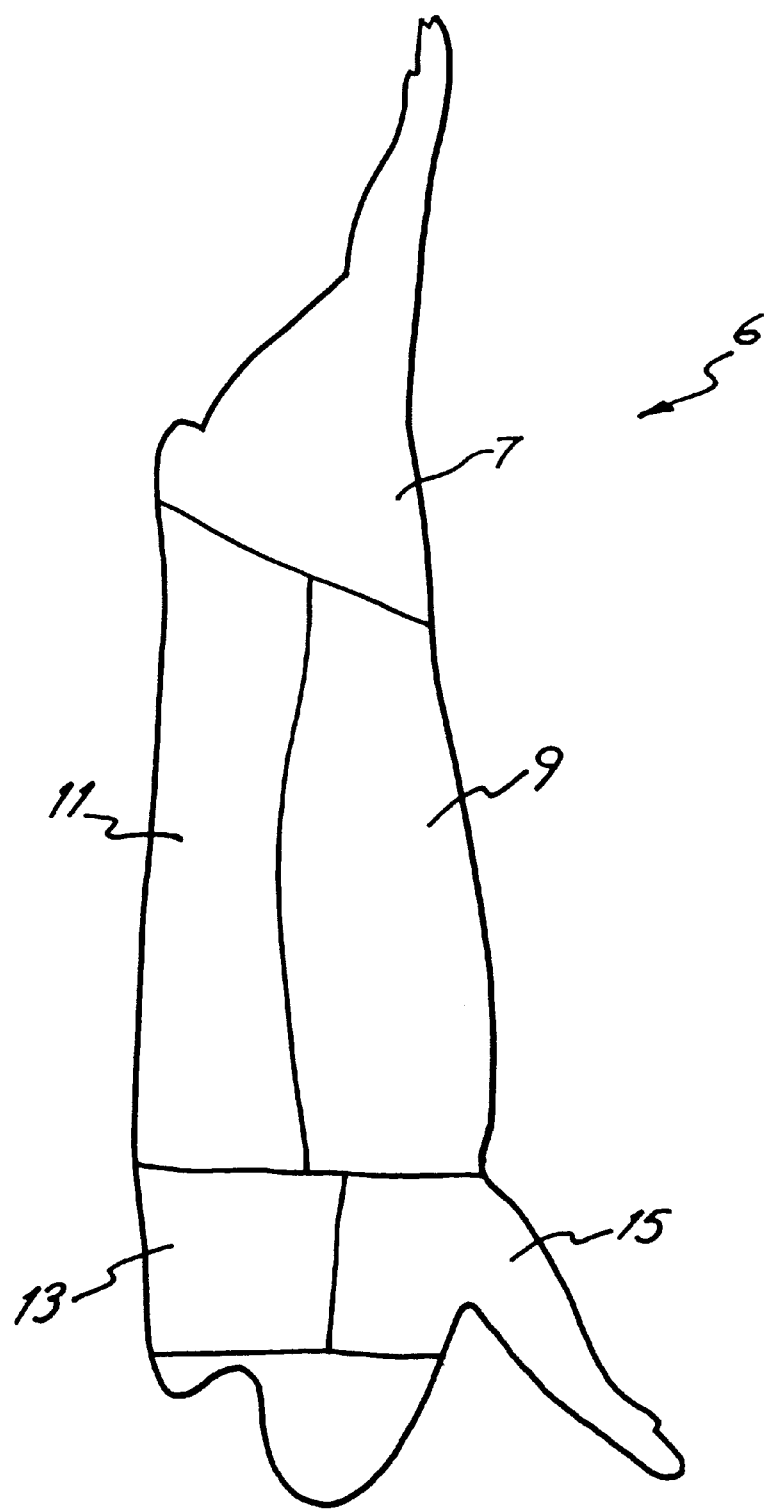
FIG. 1 is a diagram of common pork cuts.

The invention is susceptible to various modifications and alternative forms, and specifics thereof have been shown by way of example in the drawings and will be described in detail. It should be understood, however, that the intention is not to limit the invention to the particular embodiment described. On the contrary, the intention is to cover all modifications, equivalents, and alternatives falling within the spirit and scope of the invention as defined by the appended claims.

DETAILED DESCRIPTION OF THE INVENTION

The present invention is directed to a method and apparatus for determining the approximate fat content of pork bellies, and a method for categorizing pork bellies on the basis of weight and lean content. The method for determining approximate fat content includes providing a pork belly and a conductivity apparatus. The conductivity apparatus is configured and arranged to apply an electromagnetic field to the pork belly. The electromagnetic field is typically uniform and adjustable. The apparatus further includes a sensor for measuring the conductivity of the pork belly as the electromagnetic field is applied to the pork belly.

Using the conductivity measurement, the approximate fat content of the pork belly is determined on the basis of a relationship between the measured conductivity of the pork belly and the fat content of the pork belly. The approximate fat content of the pork belly is related to the measured conductivity. In certain implementations, a linear relationship between conductivity and lean content is determined. Such linear relationships allow for easy calculation of lean content. A specific measurement method includes adjusting the measured conductivity using an intercept coefficient and a correlation coefficient, such as in the following equation:

$$L = I + (C\sqrt{P})$$

wherein "L" is the approximate lean content of the pork belly in percent, "I" is the intercept coefficient from the conductivity measurement, "C" is the correlation coefficient from the conductivity measurement, and "P" is the phase mean average conductivity from the conductivity measurement. Approximate lean content is the approximate pounds of the pork belly that is not fat. Typically, the portion of the pork belly that is not fat is primarily muscle tissue and other high-protein components. Thus, a pork belly with a lean content of 70 percent is 30 percent fat and 70 percent other tissue. A pork belly with a lean content of 60 percent is 40 percent fat and 60 percent other tissue. A pork belly with a lean content of 50 percent is 50 percent fat and 50 percent other tissue. The intercept coefficient "I" is typically from about −3.0 to −2.0, frequently from about −2.1 to −2.5, and often approximately −2.35. The correlation coefficient "C" is typically from about 1.0 to 3.0, frequently from about 1.5 to 2.0, and often approximately 1.8.

The invention is also directed to a method of categorizing pork bellies. The method includes providing a plurality of pork bellies. These pork bellies are provided, for example, at a packaging plant where live hogs are butchered. A conductivity sensor is also provided and is configured and arranged to apply an electromagnetic field to individual pork bellies from the plurality of pork bellies. Each pork belly of the plurality of pork bellies is sequentially placed in the conductivity sensor; and the conductivity of each pork belly of the plurality of pork bellies is measured using the conductivity sensor. The approximate fat content of each pork belly is determined on the basis of a relationship between the measured conductivity of the pork belly and the fat content of the pork belly, and followed by categorizing each pork belly of the plurality of pork bellies on the basis of fat content and weight.

The step of providing a conductivity sensor typically includes providing a conductivity sensor having a receptacle configured to receive a pork belly; an electromagnetic field generator configured to generate an electromagnetic field through a pork belly positioned within the receptacle; and a sensor configured to measure changes in the electromagnetic field resulting from the presence of the pork belly. The receptacle can be configured to bend the pork belly upon insertion into the receptacle, or can include a receptacle configured to receive a pork belly bent into a substantially crescent shape.

In certain implementations, the method also includes measuring the weight of the pork belly and classifying the pork belly on the basis of fat content and weight. In this manner, it is possible to provide bacon producers and final consumers with a more consistent raw material based on lean percent and with enhanced information about the nature and quality of the pork bellies or bacon derived from the pork bellies. In specific implementations of the invention the pork bellies are divided into multiple groups based upon weight, and then multiple sub-groups based upon lean content. Typically, the weight categories are for a specific range of belly weights. Desirable weight ranges are from about 7 to 10 pounds, from about 10 to 12 pounds, from about 12 to 14 pounds, from about 14 to 16 pounds, from about 16 to 18 pounds, from about 18 to 20 pounds, and from 20 to 25 pounds.

These weight categories may each be divided into two or more lean content categories, desirably a high lean content and a low lean content category. In specific implementations, high lean content is greater than 65 percent, while in other implementations high lean content is greater than 60 percent, while in yet other implementations high lean content is greater than 55 percent. In certain embodiments of the invention all categories of pork bellies by weight are categorized into both high and low lean content percentages. However, in some implementations the heavier pork bellies are not divided into high and low lean content percentages because most heavier pork bellies have low lean content.

In accordance with another aspect of the invention, a method for measuring the electrical conductivity of a pork belly includes producing a substantially uniform magnetic field within a chamber having predetermined volume; causing relative movement between the pork belly and the chamber to move at least portions of the belly into and out of the chamber. The electrical conductivity of the belly is measured as the belly passes through the chamber.

In reference now to the Figures, a diagram showing various cuts of pork is shown in FIG. 1. The cuts from the pork body 6 include the ham 7, belly 9, loin 11, boston butt 13 and picnic 15. The cuts shown are given with their general dimensions, and it will be appreciated that the cuts can differ somewhat from those shown in FIG. 1.

Figure 2:
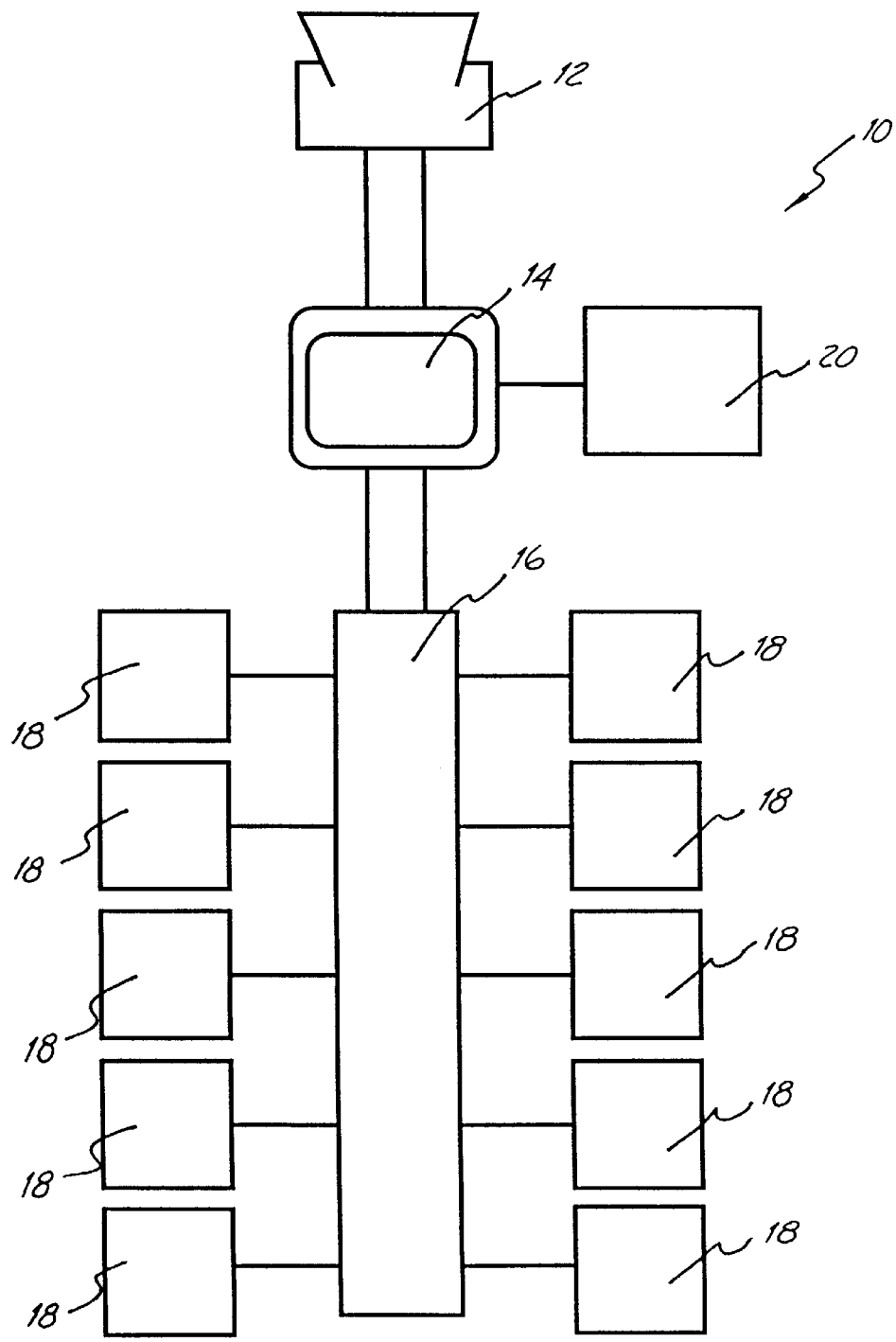
FIG. 2 is a block diagram representation of a pork belly scanning and sorting apparatus constructed in accordance with the invention.

An exemplary system for determining the lean content of a plurality of pork bellies is shown in schematic view in FIG. 2. System 10 includes a scale 12, a total body electrical conductivity measurement device 14, and an automated belly sorting device 16. The conductivity measuring device 14 for measuring conductivity may include an electrical conductivity measuring apparatus as described in U.S. Pat. No. 4,727,330 to Funk, incorporated herein by reference in its entirety. Sorting device 16 includes a plurality of pork belly receptacles 18 that receive the pork bellies based upon weight and lean content.

In operation, pork bellies sequentially pass over scale 12 and are individually weighed. Each pork belly subsequently enters conductivity measurement device 14, where the total body conductivity of the belly is measured. Based upon this measurement of the conductivity, the lean content of the belly is estimated using processor 20, which is in operational communication with scale 12, conductivity measurement device 14, and sorting device 16. Based upon weight and lean content of the pork bellies, each belly is placed into a belly receptacle 18. Each receptacle 18 can be, for example, a bin or container, or a conveyor to a person or machine who will perform further processing or packaging of the belly. In certain other implementations, the weight of each pork belly is measured after the conductivity has been measured.

Figure 3:
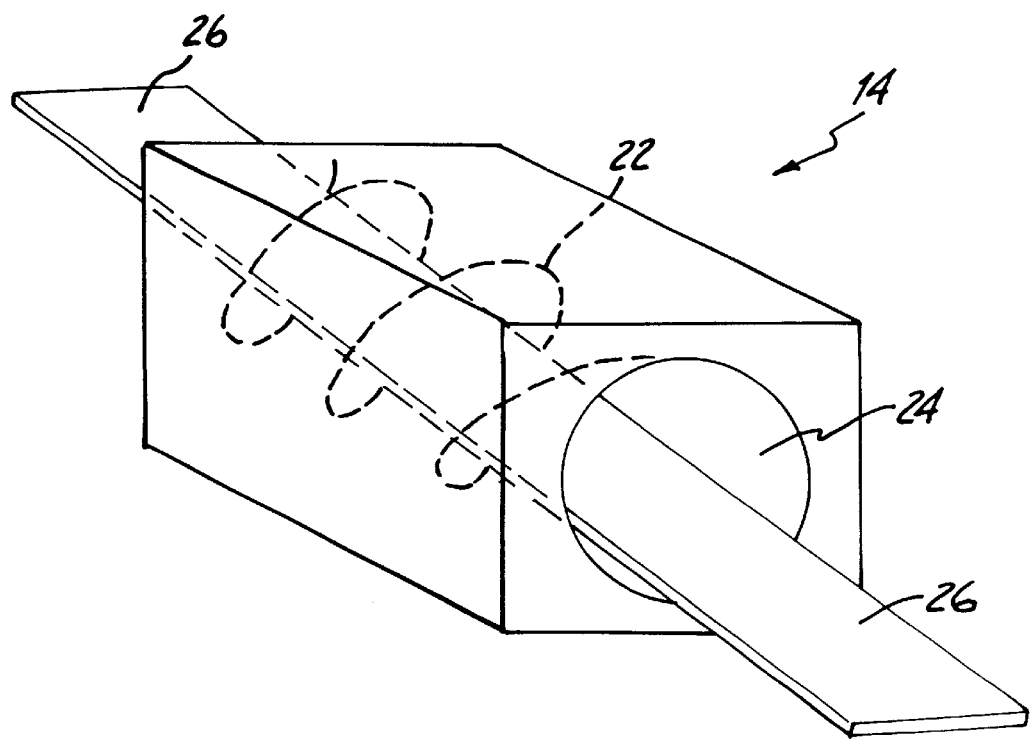
FIG. 3 is a perspective view of a conductivity scanning apparatus constructed in accordance with the invention.

In reference now to FIG. 3, the conductivity measuring device 14 may include a magnetic field source 22 that produces a substantially uniform magnetic field within a chamber 24 in conductivity measuring device 14. A conveyor apparatus 26 moves pork bellies into and out of the chamber 24. The conductivity measuring device includes a measuring circuit coupled with magnetic field source 22 for measuring the electrical conductivity. Processor 20 (from FIG. 2) controls the measuring device, and measures the electrical conductivity across the pork belly while the belly is being moved relative to chamber 24. In this manner, a plurality of measurements of the electrical conductivity of the belly can be produced.

A measuring circuit is electrically coupled with the magnetic field source 22 for measuring the electrical conductivity across the pork belly. During measurement, the belly is desirably measured at various points to determine conductivity and lean content throughout the entire belly. One method for determining only the conductivity of a portion of the belly within the chamber is by utilizing background level subtraction and a "deconvolution" process. Such background level subtraction comprises a mathematical process for taking into account the influence of factors other than the subject on the conductivity reading made across the chamber. A "convolution" of the magnetic field shape and the conductivity profile of the subject occurs during measurement due to the significant length of both the subject and the measurement fields. Measurements taken across the chamber 24 with no portion of a pork belly present will determine the background level which may then be subtracted from the measurements with the pork belly present. Similarly a measurement may be taken of the chamber 24 with a known reference element placed therein to establish the "transfer function" of the chamber 24. Once this transfer function is known, the conductivity of any object placed within the chamber 24 can be deduced by deconvoluting the resultant measurement with the known transfer function.

Figure 4:
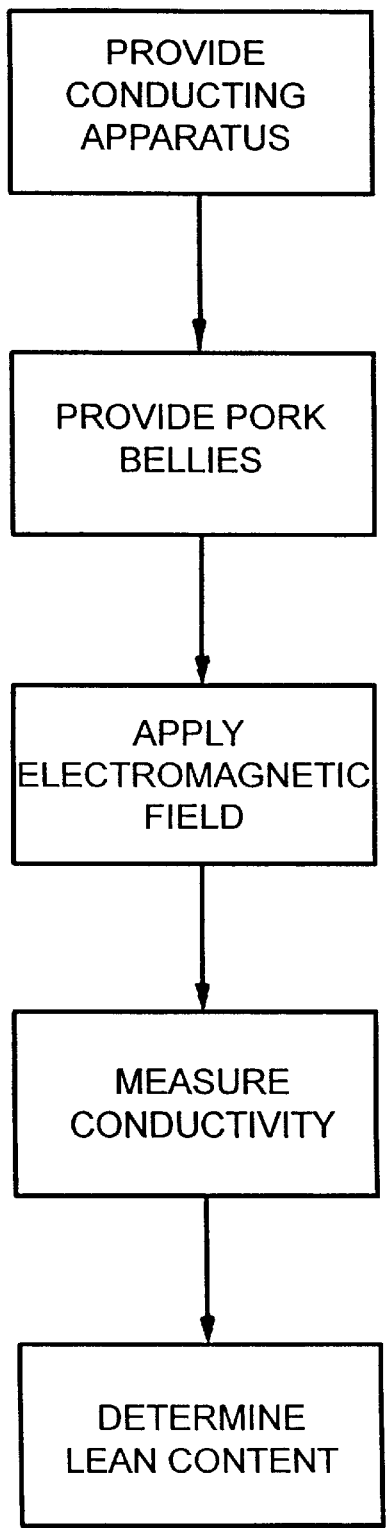
FIG. 4 is a flow chart depicting a method in accordance with the invention.

In reference now to FIG. 4, a flow chart depicting a method for determining the approximate fat content of a pork belly is shown. The method includes providing a conductivity apparatus configured and arranged to apply an electromagnetic field to a pork belly, providing a pork belly, applying an electromagnetic field to the pork belly with the conductivity apparatus, measuring the conductivity of the pork belly with the conductivity apparatus as the electromagnetic field is applied, and determining the approximate fat content of the pork belly on the basis of a relationship between the measured conductivity of the pork belly and the fat content of the pork belly.

In certain implementations, the approximate fat content of the pork belly is related to measured conductivity on the basis of the following equation:

$$L = I + (C\sqrt{P})$$

wherein "L" is the approximate lean content of the pork belly in percent, "I" is the intercept coefficient from the conductivity measurement, "C" is the correlation coefficient from the conductivity measurement, and "P" is the phase mean average conductivity from the conductivity measurement. "I" is typically from about −3.0 to −2.0, desirably from about −2.1 to −2.5, and often approximately −2.35. "C" is typically from about 1.0 to 3.0, frequently from about 1.5 to 2.0, and often approximately 1.8.

Figure 5:
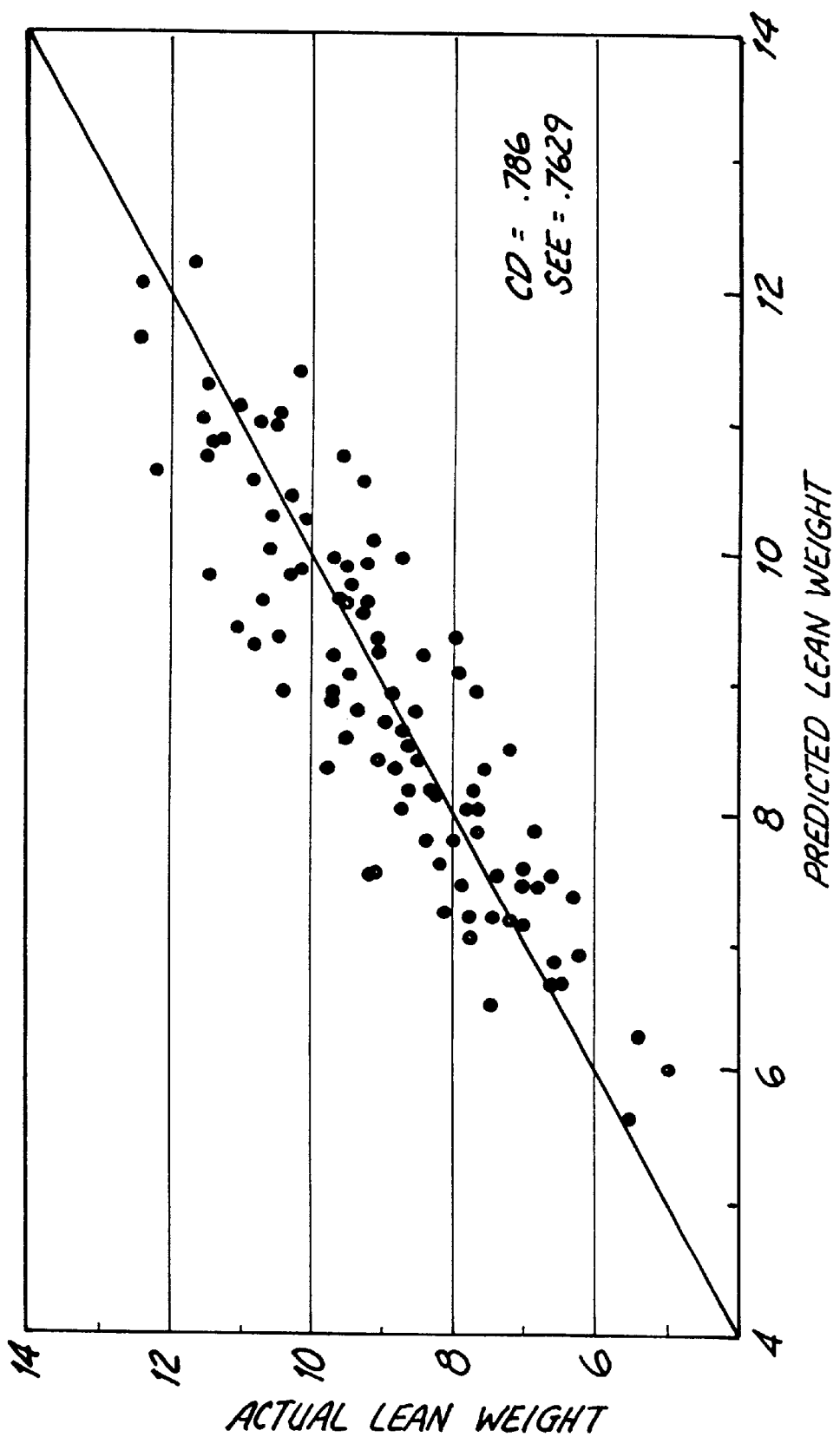
FIG. 5 is a graph showing pork belly lean content frequency in terms of actual lean content compared to predicted lean content in accordance with an implementation of the invention.

FIG. 5 shows the pork belly lean content frequency in terms of actual lean content compared to predicted lean content using total body electrical conductivity, and shows that the predicted and actual lean weight using the method of the present invention closely correlate.

The invention is also directed to a method of categorizing pork bellies. The method includes providing a plurality of pork bellies; providing a conductivity sensor configured and arranged to apply an electromagnetic field to individual pork bellies; sequentially placing each pork belly of the plurality of pork bellies into the conductivity sensor; sequentially measuring the conductivity of each pork belly of the plurality of pork bellies using the conductivity sensor; determining the approximate fat content of each pork belly on the basis of a relationship between the measured conductivity of the pork belly and the fat content of the pork belly; and categorizing each pork belly of the plurality of pork bellies on the basis of fat content. The step of providing a conductivity sensor typically includes providing a conductivity sensor having a receptacle configured to receive a pork belly; an electromagnetic field generator configured to generate an electromagnetic field through a pork belly positioned within the receptacle; and a sensor configured to measure changes in the electromagnetic field resulting from the presence of the pork belly. The receptacle can be configured to bend the pork belly upon insertion into the receptacle, or can include a receptacle configured to receive a pork belly bent into a substantially crescent shape.

The present invention has been described with reference to several particular implementations. Those skilled in the art will recognize that many changes may be made hereto without departing from the spirit and scope of the present invention. It is intended that the specification be considered as exemplary only, with the true spirit and scope of the invention being indicated by the following claims.

I claim:

1. A method of determining the approximate fat content of a pork belly, the method comprising:
   a) providing a pork belly;
   b) providing a conductivity apparatus configured and arranged to apply an electromagnetic field to the pork belly;
   c) applying an electromagnetic field to the pork belly with the conductivity apparatus;
   d) measuring the conductivity of the pork belly with the conductivity apparatus as the electromagnetic field is applied; and
   e) determining the approximate fat content of the pork belly on the basis of a relationship between the measured conductivity of the pork belly and the fat content of the pork belly.

2. The method according to claim 1, wherein the approximate fat content of the pork belly is related to measured conductivity on the basis of the following equation:

$$L = I + (C\sqrt{P})$$

wherein "L" is the approximate lean content of the pork belly in percent, "I" is the intercept coefficient from the conductivity measurement, "C" is the correlation coefficient from the conductivity measurement, and "P" is the phase mean average conductivity from the conductivity measurement.

3. The method according to claim 2, wherein "I" is between approximately −3.0 and −2.0.

4. The method according to claim 2, wherein "C" is between approximately 1.0 and 3.0.

5. The method according to claim 1, further comprising measuring the weight of the pork belly.

6. The method according to claim 1, further comprising classifying the pork belly on the basis of fat content and weight.

7. A method of categorizing pork bellies, the method comprising:
   a) providing a plurality of pork bellies;
   b) providing a conductivity sensor configured and arranged to apply an electromagnetic field to individual pork bellies;
   c) sequentially placing each pork belly of the plurality of pork bellies into the conductivity sensor;
   d) sequentially measuring the conductivity of each pork belly of the plurality of pork bellies using the conductivity sensor;
   e) determining the approximate fat content of each pork belly on the basis of a relationship between the measured conductivity of the pork belly and the fat content of the pork belly; and
   f) categorizing each pork belly of the plurality of pork bellies on the basis of fat content.

8. The method according to claim 7, wherein the step of providing a conductivity sensor comprises providing a conductivity sensor having:
   a receptacle configured to receive a pork belly;
   an electromagnetic field generator configured to generate an electromagnetic field through a pork belly positioned within the receptacle; and
   a sensor configured to measure changes in the electromagnetic field resulting from the presence of the pork belly.

9. The method according to claim 8, wherein the step of providing a receptacle comprises providing a receptacle configured to bend the pork belly upon insertion into the receptacle.

10. The method according to claim 8, wherein the step of providing a receptacle comprises providing a receptacle configured to receive a pork belly bent into a substantially crescent shape.

11. The method according to claim 7, wherein the approximate fat content of the pork belly is related to measured conductivity on the basis of the following equation:

$$L = I + (C\sqrt{P})$$

wherein "L" is the approximate lean content of the pork belly in percent, "I" is the intercept coefficient from the conductivity measurement, "C" is the correlation coefficient from the conductivity measurement, and "P" is the phase mean average conductivity from the conductivity measurement.

12. The method according to claim 11, wherein "I" is between approximately −3.0 and −2.0.

13. The method according to claim 11, wherein "C" is between approximately 1.0 and 3.0.

14. The method according to claim 7, further comprising classifying each pork belly on the basis of weight and fat content.

15. The method according to claim 14, further comprising automatically sorting each pork belly on the basis of weight and fat content.

16. A method of categorizing pork bellies, the method comprising:
   a) providing a plurality of pork bellies;
   b) providing a conductivity sensor configured and arranged to apply an electromagnetic field to individual pork bellies, the conductivity sensor comprising a receptacle configured to receive a pork belly, an electromagnetic field generator configured to generate an electromagnetic field through a pork belly positioned within the receptacle, and a sensor configured to measure changes in the electromagnetic field resulting from the presence of the pork belly;
   c) sequentially placing each pork belly of the plurality of pork bellies into the conductivity sensor;
   d) sequentially measuring the conductivity of the each pork belly of the plurality of pork bellies using the conductivity sensor; determining the approximate fat content of each pork belly on the basis of the $$L = I + (C\sqrt{P})$$

wherein "L" is the approximate lean content of the pork belly in percent, "I" is the intercept coefficient from the conductivity measurement, "C" is the correlation coefficient from the conductivity measurement, and "P" is the phase mean average conductivity from the conductivity measurement;
   e) categorizing each pork belly of the plurality of pork bellies on the basis of fat content.

17. A plurality of pork bellies sorted according to the method of claim 16.

* * * * *